United States Patent
Rot et al.

(10) Patent No.: US 10,188,341 B2
(45) Date of Patent: Jan. 29, 2019

(54) METHOD AND DEVICE FOR DETECTING SPEECH PATTERNS AND ERRORS WHEN PRACTICING FLUENCY SHAPING TECHNIQUES

(71) Applicant: Novotalk, Ltd., Givat Shmuel (IL)

(72) Inventors: Moshe Rot, Ramat Gan (IL); Lilach Rothschild, Tel Aviv (IL); Smadar Lerner, Kefar Saba (IL)

(73) Assignee: Novotalk, Ltd., Tel-Aviv (IL)

( * ) Notice: Subject to any disclaimer, the term of this patent is extended or adjusted under 35 U.S.C. 154(b) by 280 days.

(21) Appl. No.: 14/982,230

(22) Filed: Dec. 29, 2015

(65) Prior Publication Data

US 2016/0183868 A1    Jun. 30, 2016

Related U.S. Application Data

(60) Provisional application No. 62/098,355, filed on Dec. 31, 2014.

(51) Int. Cl.
  *A61B 5/00* (2006.01)
  *G09B 19/04* (2006.01)
  (Continued)

(52) U.S. Cl.
  CPC .......... *A61B 5/4803* (2013.01); *A61B 5/0022* (2013.01); *A61B 5/486* (2013.01);
  (Continued)

(58) Field of Classification Search
  CPC .................................................. A61B 5/4803
  (Continued)

(56) References Cited

U.S. PATENT DOCUMENTS 4,685,448 A    8/1987   Shames et al.
5,733,129 A    3/1998   Fayerman et al.
(Continued)

FOREIGN PATENT DOCUMENTS

EP      0887788 B1       4/2005
WO      1997001984 A1    1/1997
(Continued)

OTHER PUBLICATIONS

Simpson et al., A Practical Step-by-Step Guide to the TimeVarying Loudness Model of Moore, Glasberg and Baer (1997; 2002)., Audio Engineering Society Convention Paper 8873 Presented at the 134th Convention May 4-7, 2013 Rome, Italy.*
(Continued)

*Primary Examiner* — Thomas Hong
(74) *Attorney, Agent, or Firm* — M&B IP Analysts, LLC

(57) ABSTRACT

A method and device for detecting errors when practicing fluency shaping exercises, are presented. The method includes receiving a set of initial energy levels; setting a set of thresholds to their respective initial values; receiving a voice production of a user practicing a fluency shaping exercise; analyzing the received voice production to compute a set of energy levels composing the voice production; detecting based on the computed set of energy levels, the set of initial energy levels, and the set of a threshold of at least one speech-related error, wherein the detection of the at least one speech-related error is respective of the fluency shaping exercise being practiced by the user; and upon detection of the at least one speech-related error, generating a feedback indicating the at least one detected speech-related error.

37 Claims, 8 Drawing Sheets

(51) Int. Cl.
  *G09B 5/02*   (2006.01)
  *H04L 29/08*  (2006.01)
  *G09B 7/00*   (2006.01)
  *G06F 19/00*  (2018.01)
  *G10L 25/66*  (2013.01)
  *H04L 29/06*  (2006.01)

(52) U.S. Cl.
  CPC ............ *A61B 5/7282* (2013.01); *A61B 5/742* (2013.01); *A61B 5/7465* (2013.01); *G06F 19/00* (2013.01); *G06F 19/3418* (2013.01); *G06F 19/3481* (2013.01); *G09B 5/02* (2013.01); *G09B 7/00* (2013.01); *G09B 19/04* (2013.01); *G10L 25/66* (2013.01); *H04L 65/1069* (2013.01); *H04L 67/10* (2013.01)

(58) Field of Classification Search
  USPC ......................................................... 434/185
  See application file for complete search history.

(56) References Cited

U.S. PATENT DOCUMENTS

| | | | |
|---|---|---|---|
| 5,765,135 | A | 6/1998 | Friedman et al. |
| 5,794,203 | A | 8/1998 | Kehoe |
| 6,231,500 | B1 | 5/2001 | Kehoe |
| 6,296,489 | B1 | 10/2001 | Blass et al. |
| 7,031,922 | B1 | 4/2006 | Kalinowski et al. |
| 7,085,370 | B1 | 8/2006 | Arana-Manzano et al. |
| 7,203,649 | B1 | 4/2007 | Linebarger et al. |
| 7,258,660 | B1 | 8/2007 | Sarfati |
| 8,457,967 | B2 | 6/2013 | Audhkhasi et al. |
| 8,620,670 | B2 | 12/2013 | Malkin et al. |
| 9,826,929 | B2 | 11/2017 | Steinberg-Shapira et al. |
| 2003/0182111 | A1 | 9/2003 | Handal et al. |
| 2006/0129390 | A1 | 6/2006 | Kim et al. |
| 2006/0183964 | A1 | 8/2006 | Kehoe |
| 2007/0168187 | A1 | 7/2007 | Fletcher et al. |
| 2007/0208558 | A1 | 9/2007 | Matos |
| 2008/0271590 | A1 | 11/2008 | Lemons |
| 2009/0258333 | A1 | 10/2009 | Yu |
| 2011/0125844 | A1 | 5/2011 | Collier et al. |
| 2012/0116772 | A1* | 5/2012 | Jones .................. G06F 19/3418 704/270 |
| 2012/0244213 | A1 | 9/2012 | Emanuel |
| 2014/0038160 | A1 | 2/2014 | Shani et al. |
| 2014/0200432 | A1 | 7/2014 | Banerji et al. |
| 2014/0330557 | A1 | 11/2014 | Huber et al. |
| 2014/0342324 | A1 | 11/2014 | Ghovanloo et al. |
| 2014/0356822 | A1 | 12/2014 | Hoque et al. |
| 2015/0011842 | A1 | 1/2015 | Steinberg-Shapira |
| 2015/0118661 | A1 | 4/2015 | Haruta et al. |
| 2015/0154980 | A1 | 6/2015 | Khan et al. |

FOREIGN PATENT DOCUMENTS

| | | |
|---|---|---|
| WO | 2002041813 A1 | 5/2002 |
| WO | 2013108255 A1 | 7/2013 |
| WO | 2014042878 A1 | 3/2014 |

OTHER PUBLICATIONS

Kehoe, "Auditory Feedback Devices for Immediate Fluency," FAQ #3—Electronic Devices for Stuttering, Aug. 22, 1995.
The International Search Report and the Written Opinion of the International Searching Authority for PCT/US2015/067800, ISA/Ru, Moscow, Russia, dated Apr. 28, 2016.
The European Search Report for European Application No. 15876136.1 dated Jul. 10, 2018, EPO, Munich, Germany.
The European Search Report for European Patent Application No. 15876049.6 dated Jul. 6, 2018, EPO, Munich, Germany.
The International Search Report and The Written Opinion for PCT/US2015/067362, ISA/RU, Moscow, Russia, dated May 5, 2016.

\* cited by examiner

METHOD AND DEVICE FOR DETECTING SPEECH PATTERNS AND ERRORS WHEN PRACTICING FLUENCY SHAPING TECHNIQUES

CROSS REFERENCE TO RELATED APPLICATIONS

This application claims the benefit of U.S. provisional application No. 62/098,355 filed on Dec. 31, 2014, the contents of which are hereby incorporated by reference.

TECHNICAL FIELD

This disclosure generally relates to the field of speech teaching solutions, and more particularly to a system and methods for detecting errors in practicing fluency shaping techniques.

BACKGROUND

Speech disorders are one of the most prevalent disabilities in the world. Generally, speech disorders are classified as fluency disorders, voice disorders, motor speech disorders, and speech sound disorders. As one example, stuttering is classified as a fluency disorder in the rhythm of speech in which a person knows precisely what to say, but is unable to communicate or speak in accordance with his or her intent.

Many clinical therapy techniques for speech disorders are disclosed in the related art. Conventional techniques for treating speech disorders and, in particular, anti-stuttering techniques are commonly based on regulating the breath and controlling the rate of speech. To this end, speech therapists train their patients to improve their fluency. Such conventional techniques were found effective, in the short-term, as a speech disorder is predominantly a result of poorly coordinated speech production muscles.

In more details, one common stutter therapy technique is fluency shaping, in which a therapist trains a person (a stuttering patient) to improve his or her speech fluency through the altering of various motor skills. Such skills include the abilities to control breathing; to gently increase, at the beginning of each phrase, vocal volume and laryngeal vibration to speak slower and with prolonged vowel sounds; to enable continuous phonation; and to reduce articulatory pressure.

The speech motor skills are taught in the clinic while the therapist models the behavior and provides verbal feedback as the person learns to perform the motor skill. As the person develops speech motor control, the person increases rate and prosody of his or her speech until it sounds normal. During the final stage of the therapy, when the speech is fluent and sounds normal in the clinic, the person is trained to practice the acquired speech motor skills in his or her everyday life activities.

When fluency shaping therapy is successful, the stuttering is significantly improved or even eliminated. However, this therapy requires continuous training and practice in order to maintain effective speech fluency. As a result, the conventional techniques for practicing fluency shaping therapy are not effective for people suffering from stuttering. This is mainly because not all persons are capable of developing the target speech motor skills in the clinic, and even if such skills are developed, such skills are not easily transferable into everyday conversations. In other words, a patient can learn to speak fluently in the clinic, but will likely revert to stuttering outside of the clinic. Therefore, the continuous practicing of speech motor skills is key to successful fluency shaping therapy.

In the related art, various electronic devices are designed to improve the outcome of the anti-stuttering therapies, including fluency-shaping therapy. Examples for such devices include vocal amplitude rate-of-change device, a vocal pitch device, respiration monitors, and electromyographs (EMG). The vocal amplitude device is designed to train the loudness contour or gentle onset fluency shaping speech target.

A primary disadvantage of such devices is that they cannot be used to train patients remotely and, specifically, to remotely train speech motor skills that are essential for the success of a fluency shaping therapy. For example, the electromyography (EMG) device displays the activity of individual muscles. Using the EMG device outside of the clinics does not provide a real-time indication to the therapist of how the patient performs. Thus, the therapist cannot provide guidelines or modify the therapy session as the patient practices.

In addition, such devices are designed to aid the therapist during their therapy. As a result, a novice patient, individually practicing a fluency shaping technique cannot determine how good he or she performs. Furthermore, the currently available devices for monitoring the fluency shaping techniques are limited by their output, and in particular, outputs that can guide the user how to improve. For example, the EMG device would display the activity of individual muscles, but will not instruct the patient differently how to monitor the breathing.

In sum, the conventional solutions cannot efficiently implement procedures for fluency shaping therapy. For example, such solutions fail to provide any means for closely monitoring and providing real-time feedback to the patient practicing speech motor skills and overseeing the treatment. As another example, a patient having difficulty to perform one of the exercises may feel frustration, thereby increasing the fear and anxiety associated with patient stuttering. This would achieve the opposite effect of the desired outcome.

It would therefore be advantageous to provide an efficient solution for remote speech disorders therapy.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments, and is intended to neither identify key or critical elements of all aspects nor delineate the scope of any or all embodiments. Its sole purpose is to present some concepts of one or more embodiments in a simplified form as a prelude to the more detailed description that is presented later. For convenience, the term some embodiments may be used herein to refer to a single embodiment or multiple embodiments of the disclosure.

Certain embodiments disclosed herein include a method for detecting errors when practicing fluency shaping exercises. The method includes receiving a set of initial energy levels; setting a set of thresholds to their respective initial values; receiving a voice production of a user practicing a fluency shaping exercise; analyzing the received voice production to compute a set of energy levels composing the voice production; detecting based on the computed set of energy levels, the set of initial energy levels, and the set of a threshold of at least one speech-related error, wherein the detection of the at least one speech-related error is respective of the fluency shaping exercise being practiced by the user; and upon detection of the at least one speech-related error, generating a feedback indicating the at least one detected speech-related error.

Certain embodiments disclosed herein also include a device for detecting errors when practicing of fluency shaping exercises. The device comprises a processing unit; and a memory, the memory containing instructions that, when executed by the processing unit, configures the device to: receive a set of initial energy levels; set a set of thresholds to their respective initial values; receive a voice production of a user practicing a fluency shaping exercise; analyze the received voice production to compute a set of energy levels composing the voice production; detect based on the computed set of energy levels, the set of initial energy levels, and the set of threshold at least one speech-related error, wherein the detection of the least one speech-related error is respective of the fluency shaping exercise being practiced by the user; and upon detection of at least one speech-relate error, generate a feedback indicating the least one detected speech-related error.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

DETAILED DESCRIPTION

Figure 1:
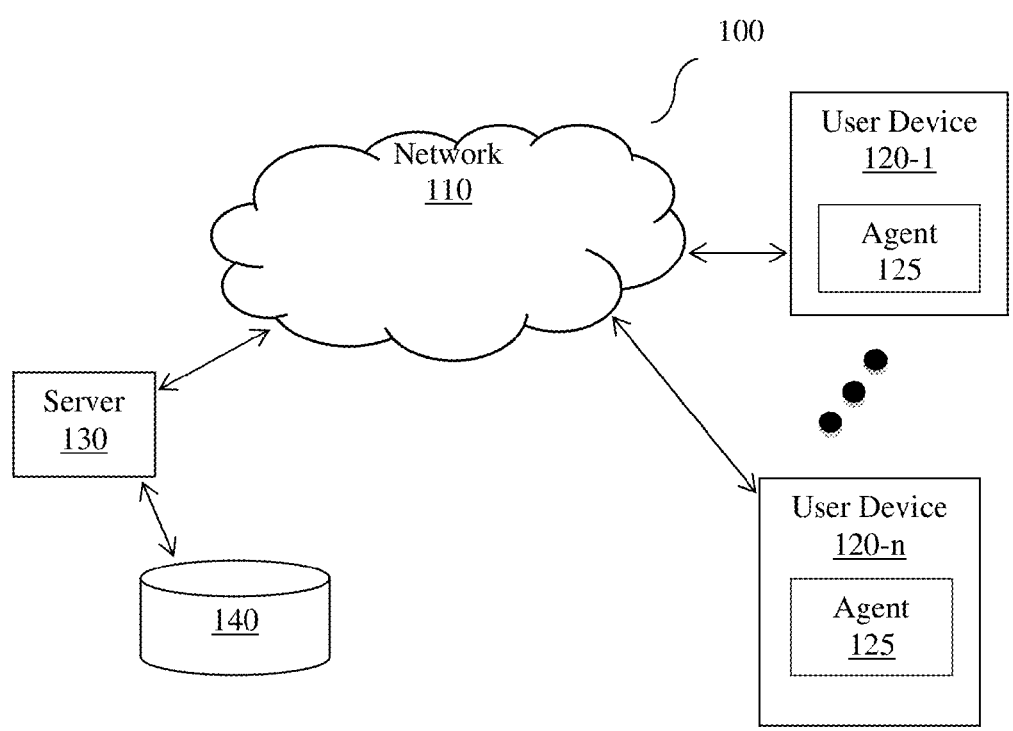
FIG. 1 is a diagram illustrating a remote speech therapy system utilized to describe the various disclosed embodiments.

It is important to note that the embodiments disclosed herein are only examples of the many advantageous uses of the innovative techniques herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

FIG. 1 shows an exemplary and non-limiting diagram of a network system 100 utilized to describe the various disclosed embodiments. The system 100 includes a network 110, a plurality of user devices 120-1 through 120-n (hereinafter referred to individually as a user device 120 and collectively as user devices 120, merely for simplicity purposes), a server 130, and a database 140.

The network 110 may be the Internet, the world-wide-web (WWW), a local area network (LAN), a wide area network (WAN), and other networks configured to communicate between the elements of the network 110. Each user device 120 may be a personal computer (PC), a personal digital assistant (PDA), a mobile phone, a smart phone, a tablet computer, a wearable computer device, a game console, and the like.

Any of the devices 120 can be utilized to practice fluency shaping techniques and/or monitor the practicing of the fluency shaping technique by another user. A non-limiting example, the user device 120-1 is utilized by a person (e.g. a stuttering patient) and the user device 120-n is utilized by a speech therapist.

According to certain implementations, each of the devices 120 is configured to communicate with the server 130. The server 130 may be configured to monitor, execute, and control a speech therapy session between the patient device 120-1 and the therapist device 120-n. The interface between the devices 120 and the server 130 may be realized through, for example, a web interface, an application installed on the devices 120, a script executed on each of the devices 120, and the like. In an embodiment, each user device 120 is installed with an agent 125 configured to perform the disclosed techniques. In certain configurations, the agent 125 can operate and be implemented as a stand-alone program and/or can communicate and be integrated with other programs or applications executed in the user device 120. Examples for a stand-alone program may include a web application, a mobile application, and the like.

The agent 125, in part under the control of the server 130, may be configured to provide an immediate feedback to the patient's performance respective of the preset target specification. Specifically, as will be discussed in greater detail below, the agent 125 is configured to conduct, monitor, analyze and report errors on various fluency shaping exercises performed by a user of a device 120. As noted above, such therapy requires exact and specific execution by the user. To this end, the agent 125 is configured to capture sound samples from the patient device 120, to analyze the sound samples, to provide an immediate visual feedback to the device 120, and to check whether the patient performance meets a predefined target template. The generated feedback can be sent to remote user device (e.g., a therapist device).

Each agent 125 ensures that the speech production is timed carefully, continued for a pre-determined amount of time, and produced in a very specific manner with a great deal of control. The visual feedbacks rendered by the agent 125 and displayed over the respective user device 120 guarantees that the patient feedback is only based on the patient's performance. The objective feedback allows the patient to speak with the required precision. The objective feedback may be realized through visual cues used to define the amount of time to prolong the syllable or word. The colors may be used to illustrate the various elements of voice production. These elements help the patient focus on producing speech that is more exact and, therefore, more correct.

A user of a user device can practice various fluency shaping techniques that can be part of a course designed to a user with speech disorders. During the course, the user (or patient) learns techniques for improving speech fluency using the system 100. The speech disorders that can be treated by practicing the techniques, as disclosed herein, may include, but are not limited to, stuttering, cluttering, diction, and others.

In order to evaluate the performance of a user practicing a fluency shaping technique, an agent 125 is configured to analyze the voice productions of the user to detect errors indicative of incorrect practicing of a specific exercise. The errors are displayed to the user as the voice productions are received. In an embodiment, the errors are displayed along with the visual representation of the voice production.

In an embodiment, the agent 125 is configured to analyze the user's performance relative to the target template. A target template predefines the specifications for performing the expected vocal productions of an exercise. The agent 125-1 is further configured to render a visual feedback respective of the user's performance, the target template, the comparisons' results, and/or any detected errors. Thus, the disclosed embodiments allow for improved effectiveness of learning a new manner of speaking which, in turn, leads to more fluent speech patterns.

According to the disclosed embodiments, the agent 125 with or without the control of the server 130, allow for practicing the fluency shaping through at least the following exercises breathing, gentle voice onset, loud voice, voice transitions, syllables rate (e.g., two seconds per syllables, one second per syllables, etc.), controlled speech, speech at a varying rate, and so on. The errors that can be detected while a user practicing these exercises include a gentle onset, a soft peak, a gentle offset, a volume control, a pattern usage, a missed of a subsequence voice production, a symmetry of the voice production, a short inhale, a too slow voice production, a too fast voice production, a too short voice production, a long voice production, and an intense peak voice production. The various embodiments for detecting such errors are discussed in greater detail below.

In an embodiment, the detected errors are reported to the server 130 and can be saved in database 140 communicatively connected to the server 130 for future usage. For example, the detected errors can be used to generate progress reports further, to determine, based on the progress reports, progress indicators such as, but not limited to, the patient's current progress level, previous successes, difficulties, and errors. Based on the determined progress indicators, the server 130 may create individualized stimuli for each practice session, thereby personalizing the experience for each user.

Figure 2:
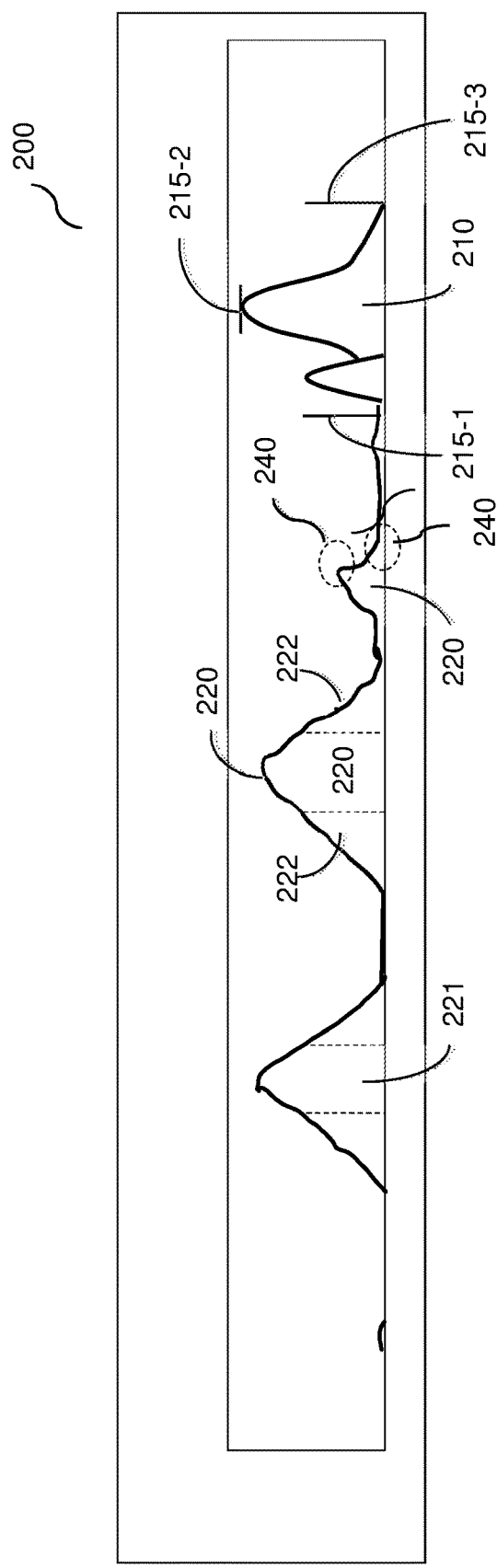
FIG. 2 is a screenshot illustrating a visual representation of a voice sound produced by a user.

Referring now to FIG. 2, which demonstrates the visual feedback and the errors displayed respective of captured voice productions. The produced voice may be visually demonstrated to provide an immediate visual feedback about the patient performance. The visual feedback may include voice coloring that is achieved by two different colors differentiating between the "softness" and "hardness" of the patient's voice. A visual feedback may include any color in the color scheme, a pattern, an image, and the like. This allows the user to better understand how the vocal cords are pressed. It should be appreciated that the immediate visual feedback, e.g., by the coloring of the voice allows self-treatment and further allows explaining the different aspects of the speech treatment. As noted above, an appropriate feedback is needed for optimal success of fluency shaping treatment.

FIG. 2 schematically illustrates a target template 210 and a visual representation 220 (voice coloring) of the voice produced by the patient. The target template 210 is displayed with a set of boundaries 215 of the target template. The boundaries 215 are dynamically determined and displayed respective of the voice production. The boundaries 215 include a start time 215-1, a finish time 215-3, and a peak 215-2 of the voice production.

The visual representation 220 includes two differently shaded portions 221 and 222, related to production of soft and loud sounds, respectively by the patient. In the example of FIG. 2, the user did not perform well and, thus, errors 240 are displayed. The errors 240 may indicate the type of errors and can provide instructions about how to improve for the next voice production, such as speaking at a lower rate, breathing before the next syllable, and so on.

It should be noted that some or all of the embodiments described above with respect to the agent 125 can equally be performed by the server 130. For example, the server 130 may receive voice samples, process the samples, and generate the visual feedbacks to the user devices 120. As another example, the server 130 may receive voice samples, process the samples, and send the processing results to the agents for rendering of the visual feedbacks.

In some implementations, each of the user devices 120 and the server 130 typically includes a processing system (not shown) connected to a memory (not shown). The memory contains a plurality of instructions that are executed by the processing system. Specifically, the memory may include machine-readable media for storing software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the one or more processors, cause the processing system to perform the various functions described herein.

The processing system may comprise or be a component of a larger processing system implemented with one or more processors. The one or more processors may be implemented with any combination of general-purpose microprocessors, microcontrollers, digital signal processors (DSPs), field programmable gate arrays (FPGAs), programmable logic devices (PLDs), controllers, state machines, gated logic, discrete hardware components, dedicated hardware finite state machines, or any other suitable entities that can perform calculations or other manipulations of information.

It should be understood that the embodiments disclosed herein are not limited to the specific architecture illustrated in FIG. 1, and other architectures may be equally used without departing from the scope of the disclosed embodiments. Specifically, the server 130 may reside in the cloud computing platform, a datacenter, and the like. Moreover, in an embodiment, there may be a plurality of servers 130 operating as described hereinabove and configured to either have one as a standby, to share the load between them, or to split the functions between them.

Figure 3:
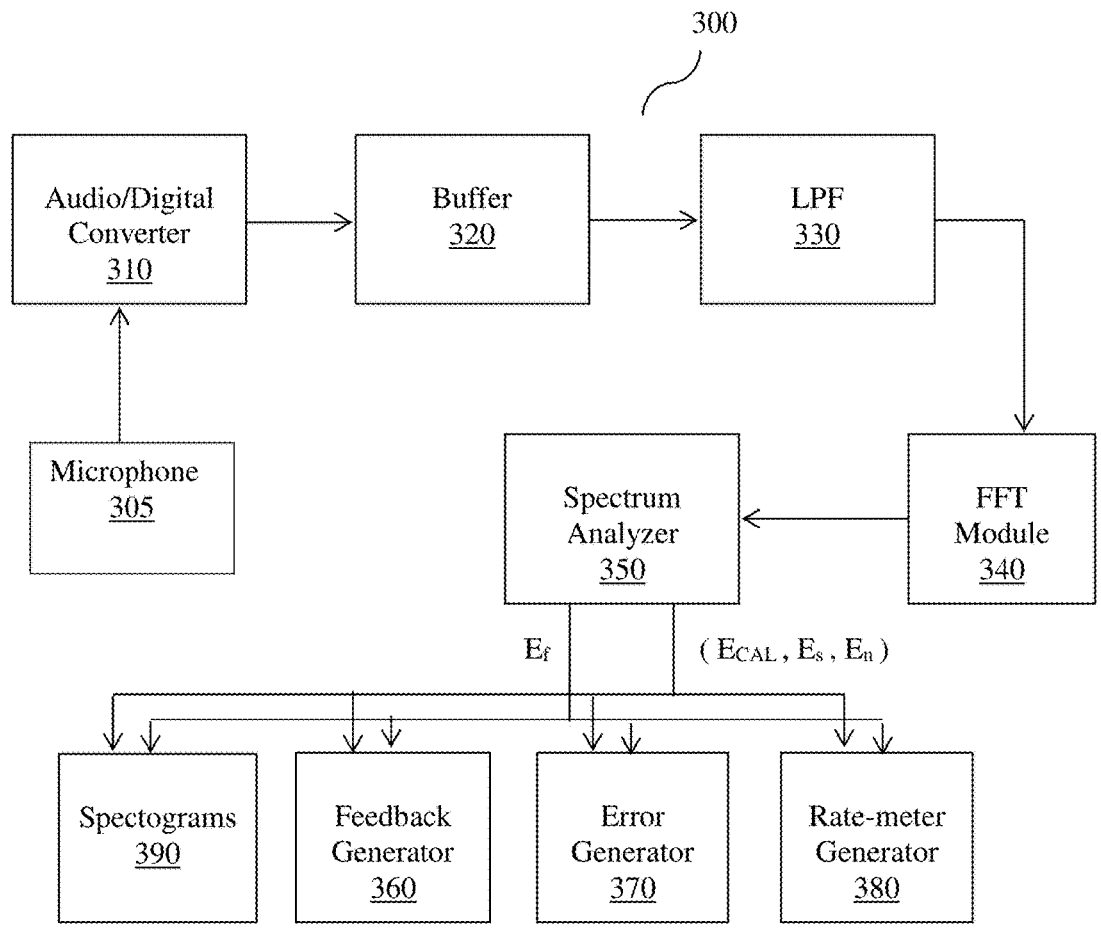
FIG. 3 is a diagram illustrating the process of detecting errors in the voice productions of a user, performing fluency-shaping exercises according to one embodiment.

FIG. 3 is a non-limiting and exemplary diagram 300 illustrating the process of detecting errors in the voice productions of a user, performing fluency-shaping exercises according to one embodiment. The process begins with audio sampling of the voice produced by a user of the system. The voice, as captured by a microphone 305, is sampled by an audio/digital converter 310. The microphone 305 may be, e.g., a microphone installed on a user device (e.g., the patient device 120-1). The sampling may be performed at a predefined rate. As a non-limiting example, the sampling rate is 800 Hz.

The voice samples produced during a predefined time interval are buffered into a buffer 320 to create voice chunks out of the samples. The duration of a single voice chunk is greater than a duration sample. In an embodiment, the size of each voice chunk may depend on a configuration of the buffer. The voice chunks may be output from the buffer at a predefined rate, for example, 10 Hz. The output voice chunks are then filtered by a low pass filter (LPF) 330 to remove or reduce any noises. In certain configurations, the LPF 330 can be applied prior to chunking of the voice samples, i.e., before the buffer 320.

The voice chunks are converted from the time domain to the frequency domain using a fast Fourier transform (FFT) module 340. Having the signals (voice chunks) in the frequency domain allows for extraction of spectrum features by a spectrum analyzer 350. Analysis of the spectrum features may be utilized to determine the quality and correctness of the voice production.

In an embodiment, the spectrum analyzer 350 extracts spectrum features that are valuable for the processing of the voice production. To this end, the zero edge frequencies may be removed and dominant frequencies may be maintained. In an embodiment, dominant frequencies are frequencies in the spectrum having an absolute amplitude level higher than a predefined threshold. In another embodiment, dominant frequencies are frequencies in the spectrum having an absolute frequency level higher than a predefined threshold. In yet another embodiment, two sets of dominant frequencies are output based on the frequencies and on the amplitudes.

The spectrum analyzer 350 computes the energy level of the dominant frequencies to output an energy level for each voice chunk. The energy may be computed as the average over the dominant frequencies. The computed energy level is represented as an integrated number. In an embodiment, the energy level can be factored by a predefined power. An exemplary energy computation may be seen in Equation 1:

$$E_f(\omega_1, \omega_2) = \beta \int_{\omega_1}^{\omega_R} |F(\omega)|^k d\omega \qquad \text{Equation 1}$$

Where, '$\omega_i$' (i=1, . . . , R) are the number of dominant frequencies in the spectrum. The factor '$\beta$' is a predefined number, while the power 'k' may be equal to or greater than 2. The computed energy level $E_f$ is of a single voice chunk and is input to a feedback generator 360, an error generator 370, and a rate-meter generator 380.

In an embodiment, the energy level ($E_s$) during a silence period (during which the patient is prompted to remain quiet) is measured or otherwise computed. Then, an energy level ($E_n$) during a normal speaking period (during which the patient is prompted to talk) is measured or otherwise computed. Finally, a calibration energy level ($E_{CAL}$) is computed as a function of the $E_n$ and $E_s$. For example, the function can be an average, a weighted average, and so on. In certain embodiments, a calibration factor received from a different device in the proximity of the patient device can be utilized in the determined $E_{CAL}$.

The feedback generator 360 plots the visual feedback respective of the voice production. The energy of each chunk is a point in the graph illustrating the voice production (for example, see FIG. 2). The feedback generator 360 colors the voice production to illustrate soft voice sounds and loud voice sounds. As noted above, two different colors (or shades) are utilized to show soft and loud voices, respectively. In an embodiment, an energy level $E_f$ of a single chuck that is below a "volume threshold" is determined to be a soft voice and an energy level $E_f$ of a single chuck that is above the volume threshold is determined to be a loud voice. The volume threshold may be determined during a calibration process of a function of energy measured during silence ($E_s$) and/or during a normal speaking of the user ($E_n$). The function can be an average or weighted average of the $E_s$ and $E_n$ values.

In a further embodiment, the feedback generator 360 dynamically sets the boundaries of the target template (shadow graph) to visually indicate to the patient when to start and end the voice production. To this end, the feedback generator 360 compares the energy level $E_f$ to the silence energy ($E_s$). When the energy level $E_f$ is greater than the silence energy ($E_s$), the beginning of a voice production may be determined, and the start and finish indicators as well as the shadowgraph may be rendered and displayed on the patient device. The finish indicator may be set to be displayed a predefined time interval after the start indicator.

The feedback generator 360 is further configured to display a breathing indicator as the voice production ends. To this end, the feedback generator 360 compares the energy level $E_f$ to the normal production energy ($E_n$). When $E_f$ is lower than $E_n$, the end of a voice production may be determined, and the breathing indicator may be rendered and displayed on the patient device.

In certain implementations, the feedback generator 360 is configured to differentiate between soft and loud voices in a voice production based on spectrum analysis of the production. In such implementations, the various energy levels determined during a calibration process may not be required.

The error generator 370 is configured to compare a voice production (between start and finish) to a respective target template. The comparison is for the entire voice production such that all computed energy levels $E_f$ of the voice chunks are buffered and analyzed to detect an error related to the production of the voice. Specifically, the detected errors are related to the patient's performance with respect to various fluency shaping exercises.

Following are non-limiting examples for errors that can be detected: a gentle onset, a soft peak, a gentle offset, a volume control, a pattern usage, a missed subsequent voice production, a symmetry of the voice production, a short inhale, a too-slow voice production, a too-fast voice production, a too-short voice production, a long voice production, a low vocal pitch, a high vocal pitch, an intense peak voice production, any combination thereof, and so on. The detected errors provide the user with an immediate feedback on how she/he may improve her/his voice production. It should be noted that, if no error is detected, a positive feedback may be provided to the user.

In certain implementations, the error generator 370 utilizes a feedback from spectrograms 390. The spectrograms 390 can be used to identify spoken words phonetically. In a particular embodiment, the spectrograms 390 can be used to identify vowels and consonants in the voice production and to compare the identified vowels and consonants to known vowels and consonants. In one configuration, the spectrograms 390 can be integrated in the error generator 370.

It should be noted that, in one embodiment, the analysis of the voice production respective of the target pattern is not a one-to-one comparison, but rather checking if the computed energy levels match the target pattern in amplitude and/or direction. In another embodiment, the analysis of the voice production respective of the target pattern is a oneto-one comparison, where matching to target template (graph) is required. In yet another embodiment, both of the comparison approaches can be utilized. The operation of the error generator 370 in detecting errors is described in more detail below.

The rate-meter generator 380 is configured to measure speech rate, for example, as a function the number of syllables per second in voice production and to render a speech rate monitor. In an embodiment, the rate-meter generator 380 operates in three ranges: controlled, slow, and normal. In order to measure the speech rate, the number of peaks of energy levels ($E_f$) in the voice production are counted, where each such peak represents a syllable. When measuring the speech rate, the duration of a voice chunk can be shortened relative to other exercises. For example, the voice chunk duration can be changed from 100 msec to 20 msec.

In certain implementations, the rate-meter generator 380 provides the measured speech rate to the error generator 370, which respective thereof determines if the speech rate diverts from a rate set of the practice of a normal conversation rate (too slow or too fast). In an embodiment, a too slow error is detected when the speech rate is below a predefined rate threshold ($TH_{rate}$). A too fast error is detected when the speech rate is above a predefined rate threshold ($TH_{rate}$). In one configuration, the rate-meter generator 380 can be integrated in the error generator 370.

The various elements discussed with reference to FIG. 3, can be implemented as hardware, firmware, software or any combination thereof and can be realized by the agent 125 (of a user device 120) and/or the server 130. When implemented, such elements may include one or more electronic circuits for processing audio signals or one or more processing systems. Examples for a processing system are provided above.

Following is a detailed discussion for detection errors related to practicing fluency shaping. A first type of error is too soft voice production. This type of error indicates that the user did not breathe out enough air when producing the voice. A correct execution of soft voice (vocal) would indicate relaxed breathing, continuous phonation, and slow, prolonged speech.

Figure 4:
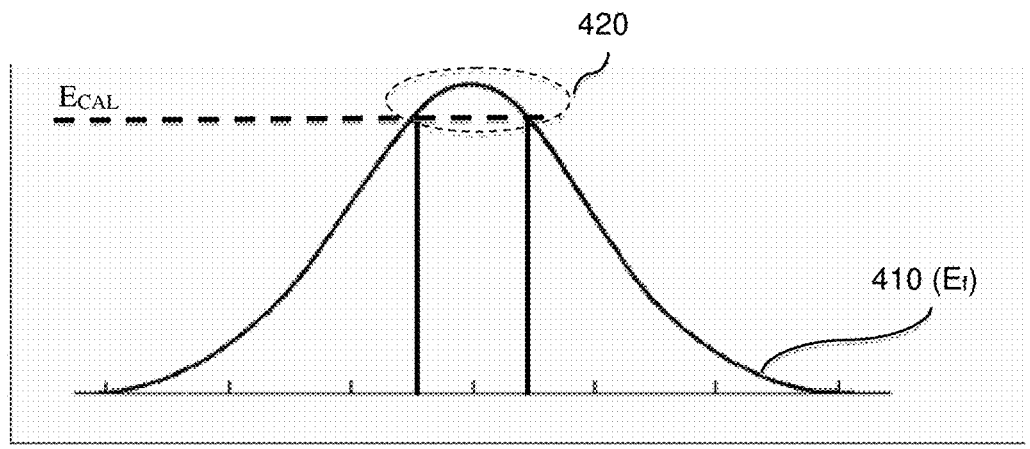
FIG. 4 is an exemplary voice production utilized to describe detection of a too soft error.

A non-limiting example for detecting a too soft error is now explained with reference to FIG. 4. The total number 410 of energy levels ($E_f$) computed during a voice production and the energy levels $E_f$ 420 above the calibration energy level $E_{CAL}$ are counted. Then, if the percentage of the energy levels $E_f$ above $E_{CAL}$ (respective of the total energy level) is below a predefined threshold (hereinafter "$TH_{soft}$"), the voice production is considered to introduce a too soft error.

In a similar manner, a too loud error is detected when the percentage of the energy levels $E_f$ above $E_{CAL}$ is below a predefined threshold (hereinafter "$TH_{loud}$"). A too loud the voice production is indicative of high articulatory muscle activity, high respiratory muscle tension, and fast speech. Typically, too loud and too soft errors are when the user is required to practice the speaking a syllable or a sequence of syllables.

Another type of error detected according to the disclosed embodiments, is the correct transitions between syllables when practicing fluency shaping. For example, of voice productions captured with respect to a user repeating word "elephant" should include transitions between three syllables "el-e-phant". The error generator 370 is configured to detect any "too soft" or "too loud" productions between such transitions. A syllable transition that is too soft or too loud indicates that the user does not efficiently control the breathing, which can lead to increased stuttering.

Figure 5:
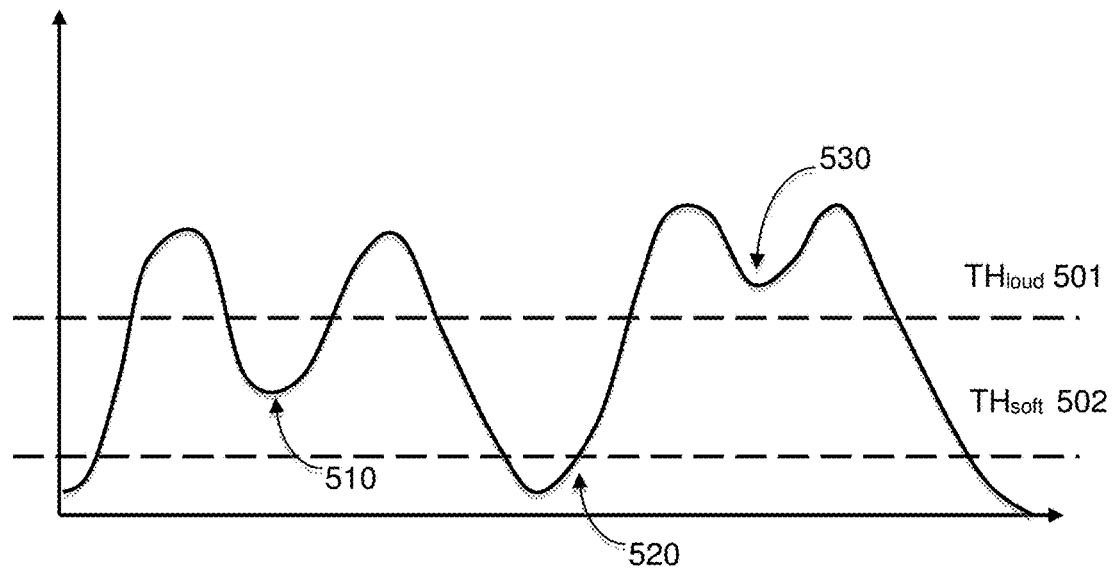
FIG. 5 is an exemplary voice production utilized to describe detection of a syllable transition error.

A non-limiting example for detecting errors in syllable transitions is now explained with reference to FIG. 5. The normal energy level ($E_n$) and silence energy level ($E_s$) are measured (or provided by a calibration process). Then, a delta energy ($\Delta E$) value between these two energy levels is computed ($E_n - E_s$). If the delta energy value ($\Delta E$) is below a soft threshold ($TH_{soft}$) 501 than the transition is too soft; if the delta energy value ($\Delta E$) is above a loud threshold 502 ($TH_{loud}$) than the transition is too loud; and if the delta energy value ($\Delta E$) is between the thresholds 501 and 502, the transition is correct. As illustrated in FIG. 5, a first transition 510 is correct, a second transition 520 is too soft, and a third transition 530 is too loud. The soft and loud thresholds are either preconfigured or set according to a calibration value. In an embodiment, transitions between too loud and too soft can be determined using the spectrograms 390.

Figure 6:
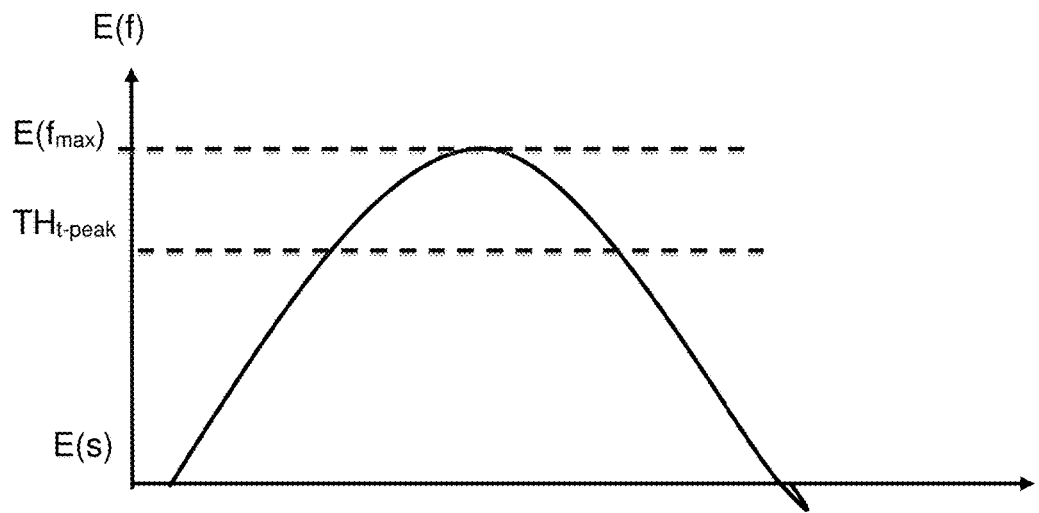
FIG. 6 is an exemplary voice production utilized to describe detection of an intense peak error.

In yet another embodiment, the error generator 370 is configured to detect an intense peak error of voice production. As illustrated in FIG. 6, an intense peak is identified when the voice production reaches an energy level ($Ef_{max}$) that is higher than a predefined time threshold ($TH_{t-peak}$). Such an error indicates that a user blows air in an uncontrolled manner when he/she produces the voice, for example, during a normal voice practice. The $TH_{t-peak}$ threshold, in an embodiment, is a function of the normal energy ($E_n$) of a normal speech as measured during a calibration process.

In another embodiment, the error generator 370 is configured to detect errors related to gentle onset and gentle offset of a voice production. A correct gentle onset (e.g., smooth increase in vocal volume at the beginning of each syllable) indicates continuous phonation. The gentle onset errors can be detected due to incorrect concaveness of the onset, a high amplitude of the onset, a length of the onset, un-gradual slope changes, and the like. Similar errors of a gentle offset production are also detected. A proper performance of gentle onset is important for fluency shaping.

Figure 7A:
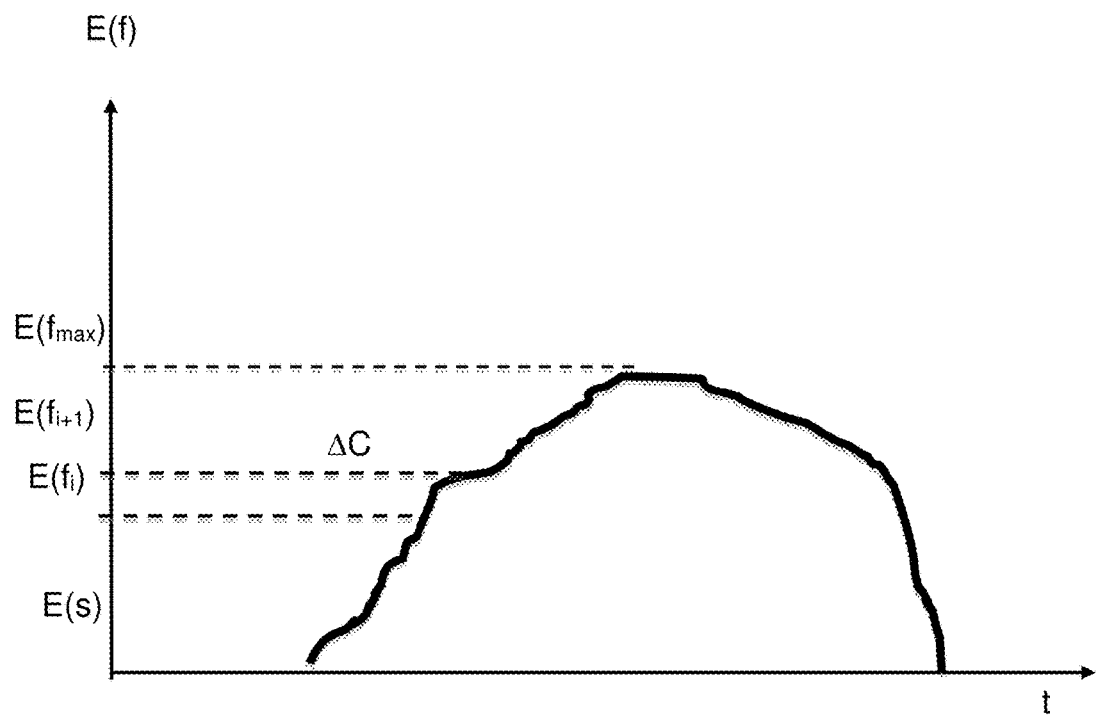
FIGS. 7A, 7B, and 7C are exemplary voice productions utilized to describe detection gentle onset errors.
Figure 7B:
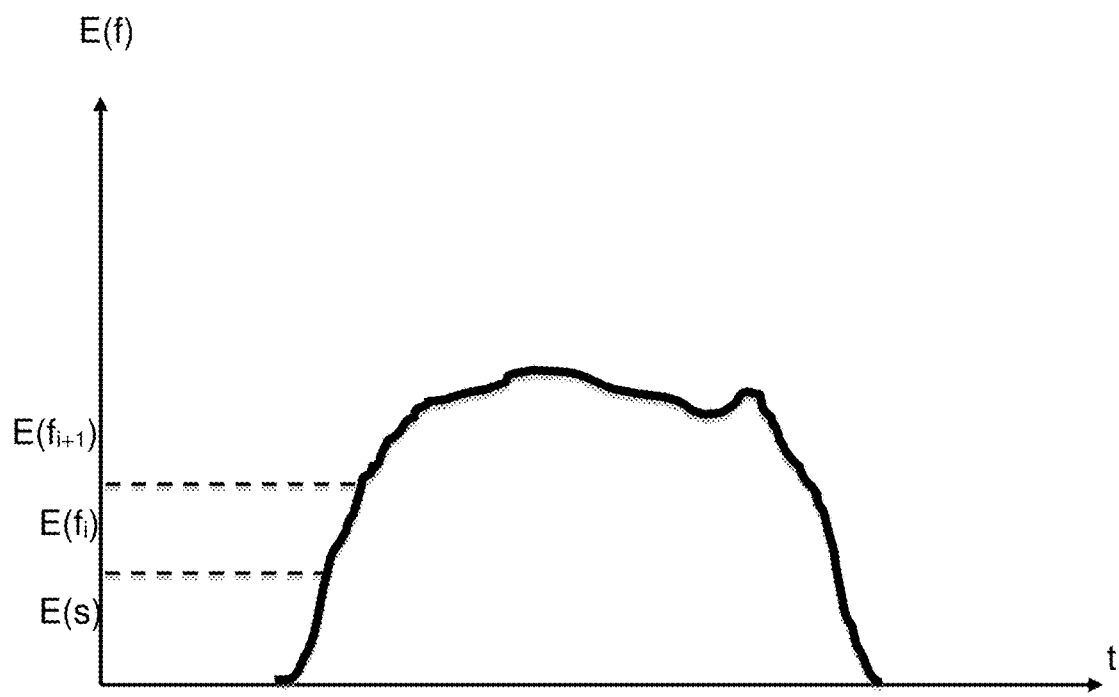
Figure 7C:
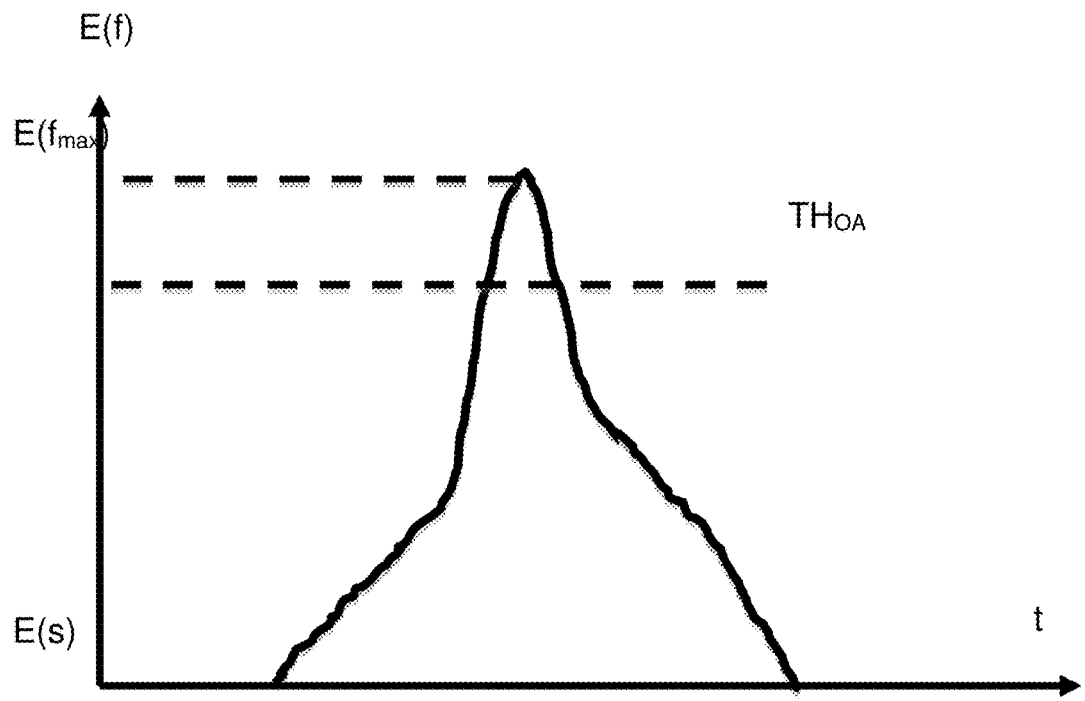

The detection of gentle onset related errors are described with reference to FIGS. 7A-7C. To identify un-gradual slope error the difference ($\Delta C$) between each two consecutive energy levels ($Ef_i$ and $Ef_{i+1}$) is computed. If the difference is greater than an onset slope threshold ($TH_{OS}$), then un-gradual slope error is detected. The threshold $TH_{OS}$, in an exemplary embodiment, is a function of the minimum ($E_s$) and maximum energy ($Ef_{max}$) levels of a voice production. The un-gradual slope error indicates a sudden change in the voice production. This error indicates that the user does not breathe in a synchronized manner, thus does not perform the fluency shaping technique well. An example for a voice production that represents an un-gradual slope error is shown in FIG. 7A.

The concaveness error is detected when the shape of the onset (of the production) is concave. This indicates that the user prolonged the speech. The concavity of the voice production is measured respective of the differences between consecutive energy levels ($Ef_i$ and $Ef_{i+1}$). An example for a voice production that represents a concaveness error is shown in FIG. 7B.

The gentle onset length is determined as a time duration from the beginning of the voice production until the peak of the production. An onset length error is detected when ratio between the onset length (T1) and the total time of the voice production (T2) is greater than a predefined threshold. That is, an onset length error is detected when the length of production is too long.

A gentle onset having a high amplitude is considered an error as the user blows more air than required in order to generate the voice production. To detect such an error, a computed or measured maximum energy level ($Ef_{max}$) of the voice production is compared to an onset amplitude threshold ($TH_{OA}$). If $Ef_{max}$ is higher than $TH_{OA}$, a high onset amplitude error is detected. An example for a voice production that represents a high onset error is shown in FIG. 7C. It should be noted that the embodiments disclosed herein for detecting gentle onset errors can equally be applied to detect gentle offset errors.

In accordance with another embodiment, volume control errors are detected. The volume control errors indicate un-continuous phonation of a syllable or phrase. Exercising control of volume of speech is important to teach the user to control his or her breathing in order to speak fluently. The volume of the voice production is detected in two vectors: power and direction. The power, or energy level is checked throughout the production to detect there are not unexpected changes in the energy levels (decrease or increase). The slope of the voice production is checked to determine any sudden changes that would change the direction of the voice production.

Figure 8:
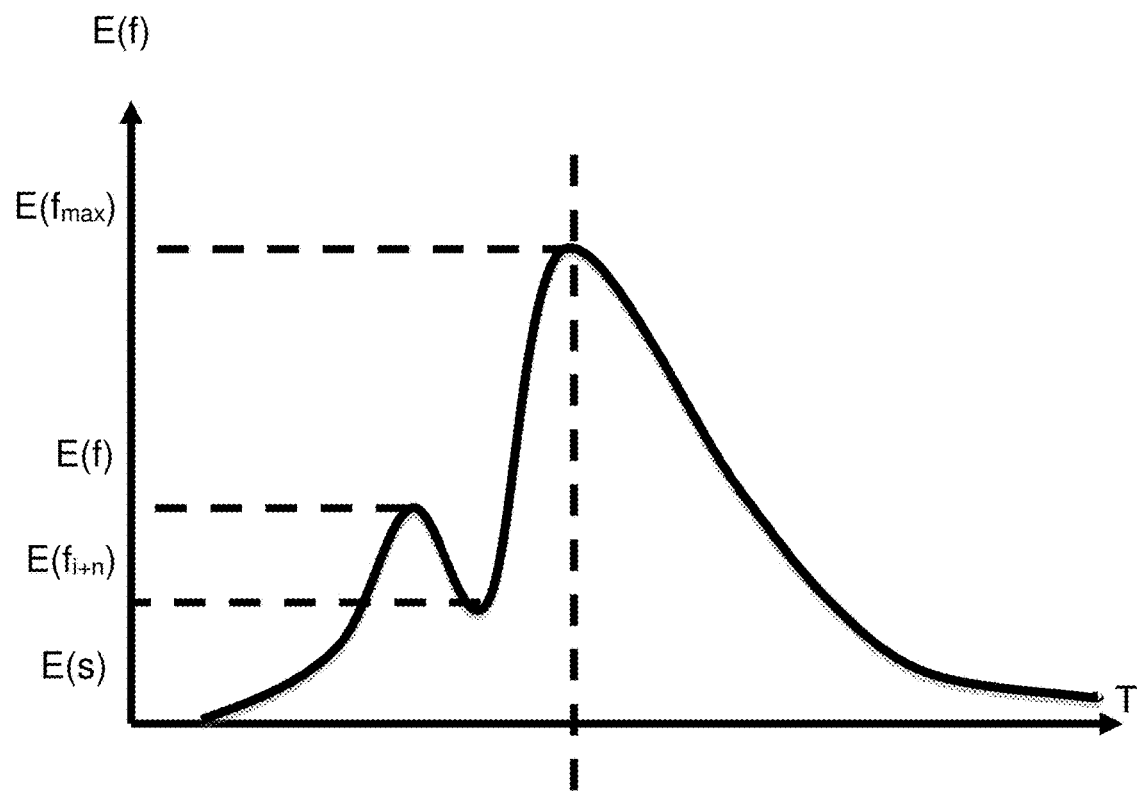
FIG. 8 is an exemplary voice production utilized to describe detection of a volume control error.

The detection of volume control related errors are described with reference to FIG. 8. The volume control error detection is by comparing each two consecutive energy levels ($Ef_i$ and $Ef_{i+1}$) from the $E_s$ level to $E_{max}$ energy levels (up direction) and from $E_{max}$ and $E_s$ energy levels (down direction). In the up direction, if the difference between two consecutive energy levels ($Ef_{i+1}$ and $Ef_i$) is a negative number (at a predefined tolerance) a volume control is detected. In a similar fashion, in the down direction if the difference $Ef_i$ and $Ef_{i+1}$ is a positive number (at a predefined tolerance), a volume control is detected. The voice production illustrated in FIG. 8 represents a volume control error in the up-direction.

Figure 9:
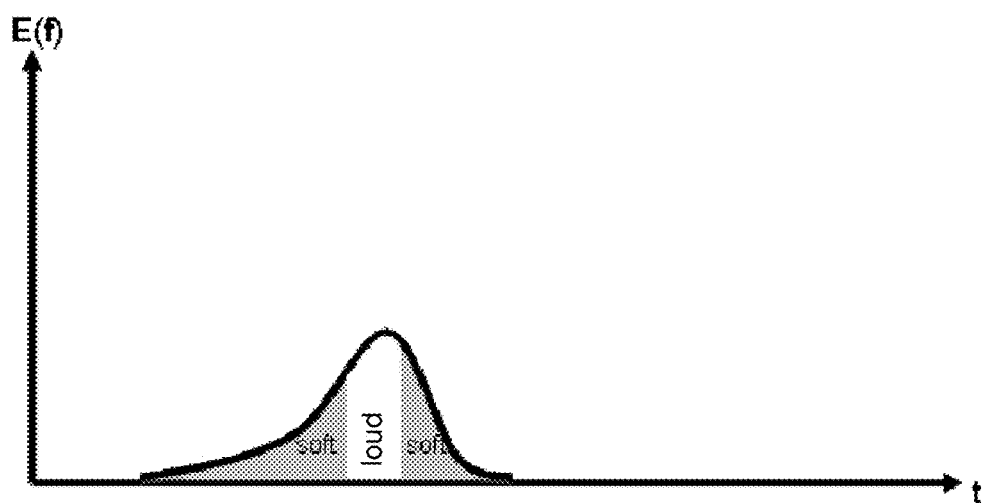
FIG. 9 is an exemplary voice production utilized to describe detection of a soft peak error.

In yet another embodiment, a soft peak error is detected for various types of voice productions when "normal" speech volume is required throughout the speech. A soft peak error is identified when a percentage of energy levels of a total of energy level is above a predefined soft peak threshold (hereinafter "$TH_{SP}$"). As noted above, the voice production is colored with two colors to show "soft" and "loud" voice, thereby allowing the user to control the production. An example for a voice production that represents a soft peak error is shown in FIG. 9.

The detection of soft peak errors can be also applied when the user is requested to generate certain patterns. The soft peak threshold ($TH_{SP}$) may be dynamically changed respective of the different patterns. A pattern can be a syllable, a word, or a sentence when the volume of the required voice production may be set from one pattern to another.

Figure 10:
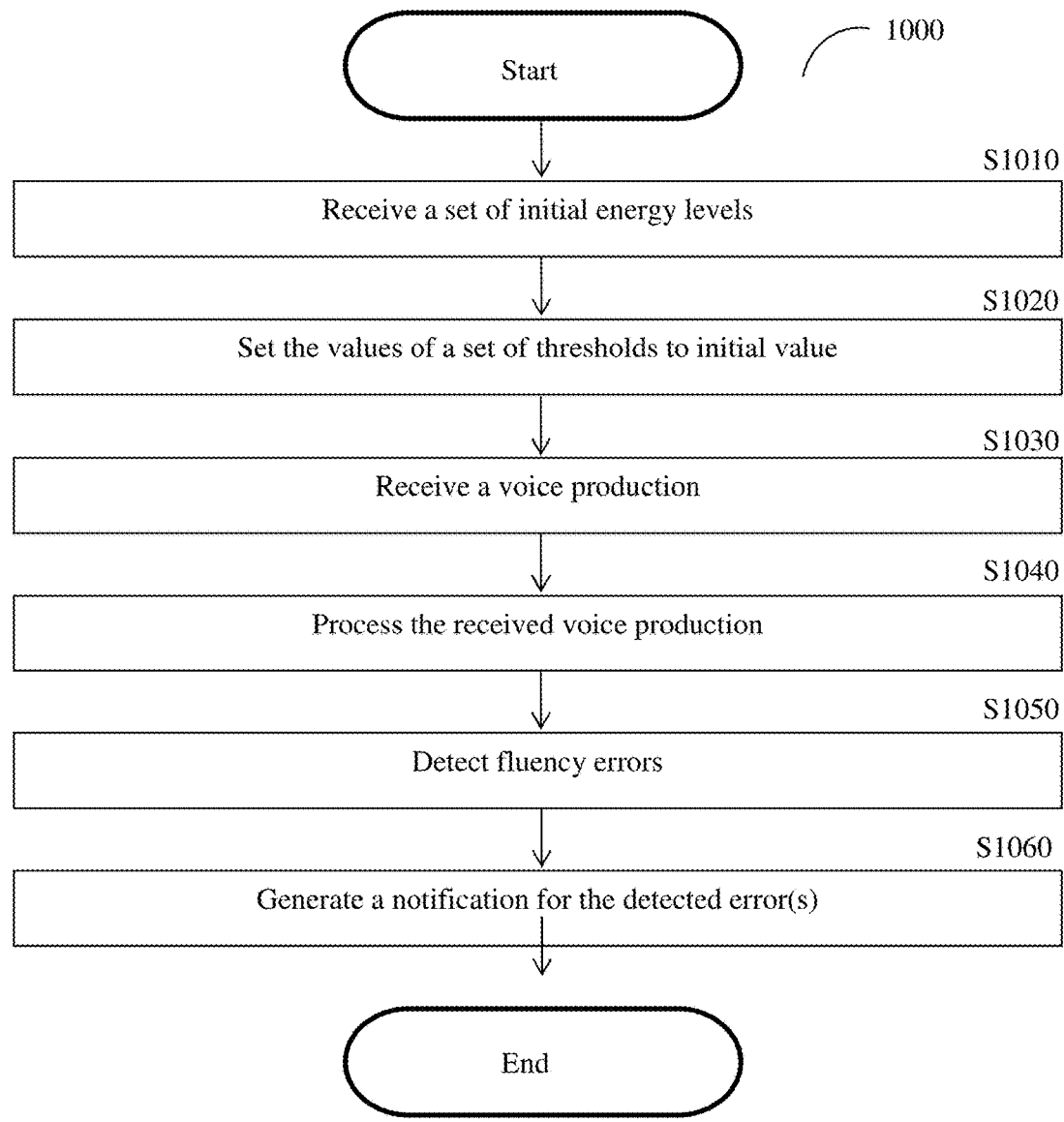
FIG. 10 is a flowchart illustrating a method for detecting errors related to practicing of fluency shaping exercises according to an embodiment.

FIG. 10 shows an exemplary and non-limiting flowchart 1000 illustrating a method for detecting errors related to the practicing of fluency shaping exercise according to one embodiment. At S1010, a set of energy levels, determined during a calibration process, are received. Such energy levels include silence ($E_s$), normal ($E_n$) and calibration ($E_{CAL}$) energy levels.

At S1020, various thresholds utilized in the detection of fluency shaping errors are set to their respective initial value. The initial value may be predefined. It should be noted that each such threshold can be later modified automatically performed by on the user performance or by a user controlling the exercise being performed. That is, all of the thresholds utilized in the detection of fluency shaping errors are configurable. As noted above, these thresholds include, for example, $TH_{soft}$ and $TH_{loud}$ for detecting too soft and loud errors, $TH_{OA}$ and $TH_{OS}$ to detect gentle onset errors, $TH_{SP}$ for detecting of soft peak errors, and $TH_{rate}$ for detecting rate errors.

At S1030, a voice production captured on the user device is received. At S1040, the received voice production is processed to measure or compute energy levels composing the voice production. The energy levels include $Ef_i$ ($i=1, \ldots, n$) where n is the number of voice chunks in the production and $Ef_{max}$.

As discussed in detail above, the processing of the voice production includes sampling the received voice production to create voice samples; buffering the voice samples to create voice chunks; converting the voice chunks from a time domain to a frequency domain; extracting spectrum features from each of the frequency domain voice chunks; measuring or computing, for each voice chunk, the energy level of the corresponding dominant frequency; and determining, for each voice chunk, an energy level of the voice chunk based on the energy level of the corresponding dominant frequency. The spectrum features include at least dominant frequencies and each dominant frequency corresponds to a voice chunk.

At S1050, using the measured the energy levels and thresholds, the fluency errors are detected. The various exemplary embodiments for detecting such errors are discussed in detail above.

At S1060, a notification with respect to a detect error is generated provided to the user. The notification may be related to the type of each detect error or preferably instruction how to improve for the next voice production. In an embodiment, the notification is in a form of a visual feedback where the error is displayed with respect to the display voice production. The visual feedback may further include coloring the voice production, displaying the voice production with respect to a target template, displaying the boundaries when to start and finish a voice production, displaying error and instructive indications, displaying breading indicators, and/or displaying a speech rate-meter.

At S1070 it is checked if any of the threshold should be modified, and if so at S1080 a threshold can be modified and execution returns to S1030. Otherwise, execution terminates. It should be noted that modification of a threshold may be required, for example, to reduce the difficulty of a certain exercise. For example, upon detection repeating errors of the same user.

It should be appreciated that the qualitative analysis of the patient's performance of the various exercises allows determination of the types of errors and difficulties that the patient repeatedly has. This determination allows for creation of a personalized treatment program that would encourage review of content as needed and match the stimuli in the exercise to the specific difficulties the user is experiencing.

The steps of the method 1000 are shown in a specific order merely for simplicity purposes and without limitation on the disclosed embodiments. The method steps can be performed in different sequences without departing from the scope of the disclosure. Any or all of the steps of the method 1000 may be repeated, preferably in response to user inputs indicating a desire to revisit one or more of the steps.

The various embodiments disclosed herein can be implemented as hardware, firmware, software or any combination thereof. Moreover, the software is preferably implemented as an application program tangibly embodied on a program storage unit, a non-transitory computer readable medium, or a non-transitory machine-readable storage medium that can be in a form of a digital circuit, an analog circuit, a magnetic medium, or combination thereof. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such computer or processor is explicitly shown. In addition, various other peripheral units may be connected to the computer platform such as an additional data storage unit and a printing unit. Furthermore, a non-transitory computer readable medium is any computer readable medium except for a transitory propagating signal.

While the disclosed embodiments have been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the disclosure. Furthermore, the foregoing describes the disclosure in terms of embodiments foreseen by the inventor for which an enabling description was available, notwithstanding that insubstantial modifications of the disclosed embodiments, not presently foreseen, may nonetheless represent equivalents thereto.

What is claimed is:

1. A method for detecting errors when practicing fluency shaping exercises, comprising:
   receiving a set of initial energy levels;
   setting each threshold of a set of thresholds to a respective predetermined initial value;
   receiving a voice production of a user practicing a fluency shaping exercise;
   analyzing the received voice production to compute a set of energy levels composing the voice production;
   detecting at least one speech-related error based on the computed set of energy levels, the set of initial energy levels, and the set of a thresholds, wherein the detection of the at least one speech-related error is with respect to the fluency shaping exercise being practiced by the user; wherein the set of initial energy levels includes at least one of: a normal speech energy level, a silence energy level, and a calibration energy level,
   upon detection of the at least one speech-related error, generating visual feedback indicating the at least one detected speech-related error with respect to the received voice production, and
   performing an audio calibration process for a computing device of the user to set the normal speech energy level, the silence energy level, and the calibration energy level, wherein the voice production is captured on the computing device of the user,
   wherein processing the received voice production further comprises: sampling the received voice production to create voice samples; buffering the voice samples to create voice chunks; converting the voice chunks from a time domain to a frequency domain; extracting spectrum features from each of the frequency domain voice chunks, wherein the spectrum features include at least dominant frequencies, wherein each dominant frequency corresponds to a voice chunk; computing, for each voice chunk, the energy level of the corresponding dominant frequency; and determining, for each voice chunk, an energy level of the voice chunk based on the energy level of the corresponding dominant frequency.

2. The method of claim 1, wherein the set of initial energy levels includes a calibration energy level, wherein detecting the at least one speech-related error further comprises: checking if a percentage of a total of computed energy levels above the calibration energy level is below an initial value of a too soft threshold, wherein the too soft threshold is one of the set of the thresholds; and detecting a too soft error voice production when the percentage is below the initial value of the too soft threshold.

3. The method of claim 2, wherein detecting the at least one speech-related error further comprises:
   checking if the percentage of the total of computed energy levels above the calibration energy level is above an initial value of a too loud threshold, wherein the too loud threshold is one of the set of thresholds; and
   detecting a too loud error voice production when the percentage is above the initial value of the too loud threshold.

4. The method of claim 3, wherein the set of initial energy levels includes a normal speech enemy level and a silence energy level, wherein detecting the at least one speech-related error further comprises:
   computing an energy difference between the normal speech energy level and the silence energy level;
   comparing the energy difference to the too loud threshold and the too soft threshold; and
   detecting a syllable transition error when the computed difference is below the too loud threshold and the too soft threshold.

5. The method of claim 1, wherein the set of initial energy levels includes a normal speech energy level, wherein detecting the at least one speech-related error further comprises: determining a maximum energy level out of the measured energy levels of the voice production; checking if the maximum energy level is above an initial value of an intense peak threshold, wherein an initial value the intense peak threshold is set respective of the normal speech energy level, wherein the intense peak threshold is one of the set of the thresholds; and detecting an intense peak threshold error voice production when the maximum energy level is above the initial value of an intense peak threshold.

6. The method of claim 1, wherein the set of initial energy levels includes a normal speech energy level and a silence energy level, further comprising: computing an energy difference between each two consecutive energy levels; comparing the energy difference to an initial value of an onset slope threshold, wherein an initial value the onset slope threshold is set respective of the silence energy level and a maximum energy level, wherein the onset slope threshold is one of the set of the thresholds; detecting an un-gradual slope gentle onset speech error, when the computed energy difference is above the initial value of the onset slope threshold.

7. The method of claim 1, further comprising: determining a maximum energy level out of the measured energy levels of the voice production; comparing the energy difference to an initial value of an onset amplitude threshold, wherein the onset amplitude threshold is one of the set of thresholds; detecting a high amplitude gentle onset speech error, when the maximum energy level is above the initial value of the onset amplitude threshold.

8. The method of claim 7, wherein the detected speech-related error further includes any one of: a too-long gentle onset and a concave gentle onset.

9. The method of claim 1, wherein the detected speech-related error further includes any one of: a too-long gentle offset, an un-gradual slope gentle offset, a high amplitude gentle offset, and a concave gentle offset.

10. The method of claim 1, wherein the set of initial energy levels includes a silence energy level, further comprising: determining a maximum energy level out of the measured energy levels of the voice production; computing an energy difference between each two consecutive energy levels from the silence energy level to the maximum energy level; and detecting a volume control speech error, when the energy difference is negative.

11. The method of claim 1, wherein the set of initial energy levels includes a silence energy level, further comprising: determining a maximum energy level out of the measured energy levels of the voice production; computing an energy difference between each two consecutive energy levels from the maximum energy level to the silence energy level; and detecting a volume control speech error, when the energy difference is positive.

12. The method of claim 1, further comprising: checking if a first number of the computed energy levels out of a total of computed energy levels is above an initial value of a soft peak threshold, wherein the soft peak threshold is one of the set of the thresholds; and detecting a soft peak error voice production when the first number of the computed energy levels is above the soft peak threshold.

13. The method of claim 1, further comprising:
measuring a speech rate respective of the analysis; and
detecting a speech rate error when the measured speech rate is below an initial value of a rate threshold, wherein the rate threshold is one of the set of thresholds and set to indicate a normal speech rate.

14. The method of claim 1, further comprising:
sending the generated feedback to a computing device of the user for display.

15. The method of claim 14, wherein generating the feedback further comprises:
coloring the voice production using at least a first color and a second color, wherein the first color represents a loud sound produced by the user and the second color represents a soft sound produced by the user.

16. The method of claim 1, wherein the at least one exercise includes a sequence of voice productions.

17. The method of claim 1, further comprising:
generating a report summarizing the execution of the voice production throughout a current therapy session; and
saving the report.

18. The method of claim 1, wherein the fluency shaping exercise is being practiced during a speech disorder therapy, the speech disorder therapy is used for at least one of: stuttering, cluttering, and diction.

19. A non-transitory computer readable medium having stored thereon instructions for causing one or more processing units to execute the method according to claim 1.

20. A device for detecting errors when practicing of fluency shaping exercises, comprising:
a processing unit; and
a memory, the memory containing instructions that, when executed by the processing unit, configures the device to:
receive a set of initial energy levels, wherein the set of initial energy levels include at least one of: a normal speech energy level, a silence energy level, and a calibration energy level;
set each threshold of a set of thresholds to a respective predetermined initial value;
receive a voice production of a user practicing a fluency shaping exercise;
analyze the received voice production to compute a set of energy levels composing the voice production;
detect at least one speech-related error based on the computed set of energy levels, the set of initial energy levels, and the set of thresholds, wherein the detection of the least one speech-related error is with respect to the fluency shaping exercise being practiced by the user; and
upon detection of at least one speech-relate error, generate a-visual feedback indicating the least one detected speech-related error with respect to the received voice production,
wherein the device is further configured to: perform an audio calibration process for a computing device of user to set the normal speech energy level, the silence energy level, and the calibration energy level, wherein the voice production is captured on a computing device of the user, and
wherein the device is further configured to: sample the received voice production to create voice samples; buffer the voice samples to create voice chunks; convert the voice chunks from a time domain to a frequency domain; extract spectrum features from each of the frequency domain voice chunks, wherein the spectrum features include at least dominant frequencies, wherein each dominant frequency corresponds to a voice chunk; compute, for each voice chunk, the energy level of the corresponding dominant frequency; and determine, for each voice chunk, an energy level of the voice chunk based on the energy level of the corresponding dominant frequency.

21. The device of claim 20, wherein the set of initial energy levels includes a calibration energy level, wherein the device is further configured to: check if a percentage of a total of computed energy levels above the calibration energy level is a below an initial value of a too-soft threshold, wherein the too soft threshold is one of the set of thresholds; and detect a too-soft error voice production when the percentage is below the initial value of the too-soft threshold.

22. The device of claim 20, wherein the device is further configured to: check if a percentage of a total of computed energy levels above the calibration energy level is a above an initial value of a too-loud threshold, wherein the too-loud threshold is one of the set of the thresholds; and detect a too loud error voice production when the percentage is above initial value of the too-loud threshold.

23. The device of claim 22, wherein the set of initial energy levels includes a normal speech energy level and a silence energy level, wherein the device is further configured to: compute an energy difference between the normal energy level and the silence energy level; compare the energy difference to the too-loud threshold and the too soft threshold; and detect a syllable transition error when the computed difference is below the too-loud threshold and the too-soft threshold.

24. The device of claim 20, wherein the set of initial energy levels includes a normal speech energy level, wherein the device is further configured to: determine a maximum energy level out of the measured energy levels of the voice production; check if the maximum energy level is above an initial value of an intense peak threshold, wherein an initial value the intense peak threshold is set respective of the normal energy level, the intense peak threshold is one of the set of the thresholds; and detect an intense peak threshold error voice production when the maximum energy level is above the initial value of an intense peak threshold.

25. The device of claim 20, wherein the set of initial energy levels includes a normal speech energy level and a silence energy level, wherein the device is further configured to: compute an energy difference between each two consecutive energy levels; compare the energy difference to an initial value of an onset slope threshold, wherein an initial value the onset slope threshold is set respective of the silence energy level and a maximum energy level, the onset slope threshold is one of the set of the thresholds; detect an un-gradual slope gentle onset speech error, when the computed energy difference is above the initial value of the onset slope threshold.

26. The device of claim 20, wherein the device is further configured to: determine a maximum energy level out of the measured energy levels of the voice production; compare the energy difference to an initial value of an onset amplitude threshold, wherein the onset amplitude threshold is one of the set of the thresholds; detect a high amplitude gentle onset speech error, when the maximum energy level is above the initial value of the onset amplitude threshold.

27. The device of claim 26, wherein the detected speech-related error further includes any one of: a too long gentle onset and a concave gentle onset.

28. The device of claim 20, wherein the detected speech-related error further includes any one of: a too long gentle offset, an un-gradual slope gentle offset, a high amplitude gentle offset, and a concave gentle offset.

29. The device of claim 20, wherein the set of initial energy levels includes a silence energy level, wherein the device is further configured to: determine a maximum energy level out of the measured energy levels of the voice production; compute an energy difference between each two consecutive energy levels from the silence energy level to maximum energy level; and detect a volume control speech error when the energy difference is negative.

30. The device of claim 20, wherein the set of initial energy levels includes a silence energy level, wherein the device is further configured to: determine a maximum energy level out of the measured energy levels of the voice production; compute an energy difference between each two consecutive energy levels from the maximum energy level to the silence energy level; and detect a volume control speech error, when the energy difference is positive.

31. The device of claim 20, wherein the device is further configured to: check if a first number of the computed energy levels out of a total of computed energy levels is above an initial value of a soft peak threshold, wherein the soft peak threshold is one of the set of the thresholds; and detect a soft peak error voice production when the first number of the computed energy levels is above the soft peak threshold.

32. The device of claim 20, wherein the device is further configured to:
measure a speech rate respective of the analysis; and
detect a speech rate error when the measured speech rate is below initial an value of a rate threshold, wherein the rate threshold is one of the set of thresholds and set to indicate a normal speech rate.

33. The device of claim 20, wherein the device is further configured to:
send the generated feedback to a computing device of the user for display.

34. The device of claim 33, wherein generating the feedback further comprises:
coloring the voice production using at least a first color and a second color, wherein the first color represents a loud sound produced by the user and the second color represents a soft sound produced by the user.

35. The device of claim 20, wherein the at least one exercise includes a sequence of voice productions.

36. The device of claim 20, wherein the device is further configured to:
generate a report summarizing the execution of the voice production throughout the current therapy session; and
save the report.

37. The device of claim 20, wherein the fluency shaping exercise is being practiced during a speech disorder therapy, the speech disorder therapy is used for at least one of: stuttering, cluttering, and diction.

* * * * *